US005570425A

United States Patent [19]

Goodman et al.

[11] Patent Number: 5,570,425

[45] Date of Patent: Oct. 29, 1996

[54] TRANSDUCER DAISY CHAIN

[75] Inventors: Seth D. Goodman; Larry J. Eriksson, both of Madison; Douglas E. Melton, Stoughton; Edward R. Braun, Madison, all of Wis.

[73] Assignee: Digisonix, Inc., Middleton, Wis.

[21] Appl. No.: 335,456

[22] Filed: Nov. 7, 1994

[51] Int. Cl.[6] ............................ A61F 11/06; H03B 29/00

[52] U.S. Cl. ................................ 381/71; 381/94; 381/72

[58] Field of Search ................................ 381/71, 94, 72

[56] References Cited

U.S. PATENT DOCUMENTS

| | | | |
|---|---|---|---|
| 4,677,676 | 6/1987 | Eriksson | 381/71 |
| 4,677,677 | 6/1987 | Eriksson | 381/71 |
| 4,815,139 | 3/1989 | Eriksson et al. | 381/71 |
| 5,216,721 | 6/1993 | Melton | 381/71 |
| 5,216,722 | 6/1993 | Popovich | 381/71 |

FOREIGN PATENT DOCUMENTS

| | | | |
|---|---|---|---|
| 402137600 | 5/1990 | Japan | 381/71 |
| 2271908 | 4/1994 | United Kingdom | 381/71 |

OTHER PUBLICATIONS

Reza S. Raji, Entitled "Smart Networks For Control", IEEE Spectrum Jun. 1994, pp. 49–55.

*Primary Examiner*—Curtis Kuntz
*Assistant Examiner*—Minsun Oh
*Attorney, Agent, or Firm*—Andrus, Sceales, Starke & Sawall

[57] ABSTRACT

An adaptive multi-channel active acoustic attenuation system is provided for attenuating complex acoustic waves. The system includes a plurality of input sensor nodes and a plurality of error sensor nodes. Each node includes a central processing unit and a network interface. A medium physically interconnects each of the network interfaces to a communication module of a controller by means of a control bus or the like. A control network is provided for controlling communication between a communication module of a controller and each of the network interfaces to control the flow of data along the medium.

21 Claims, 6 Drawing Sheets

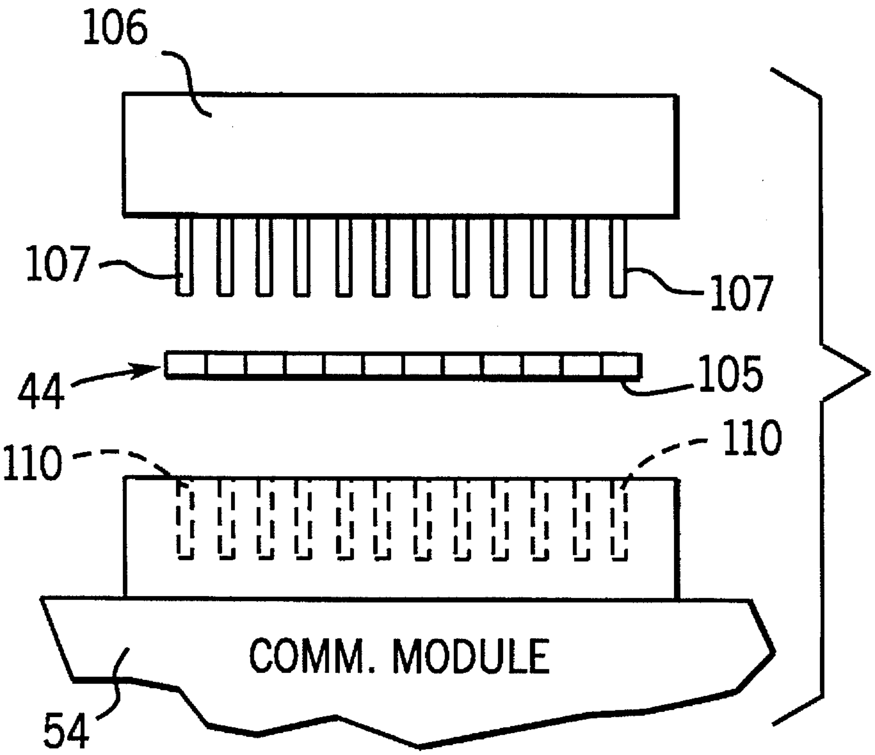
FIG. 9
FIG. 10
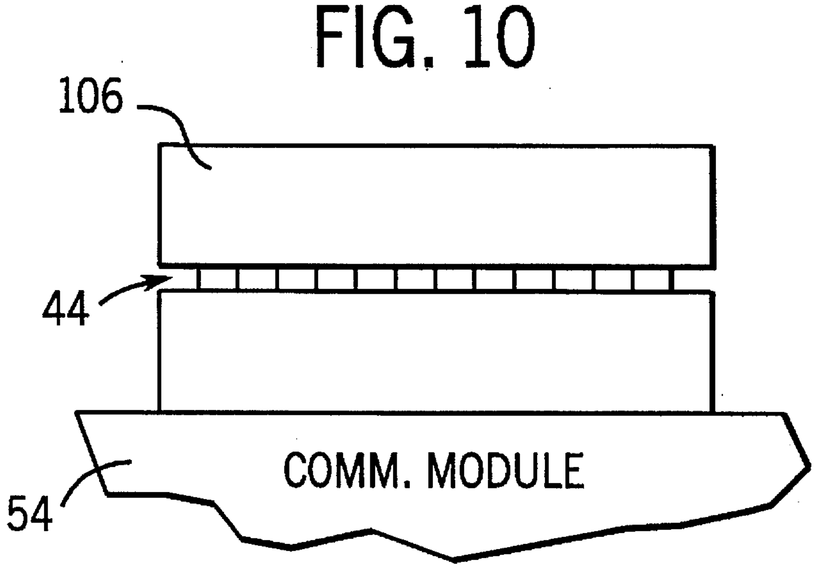

TRANSDUCER DAISY CHAIN

BACKGROUND OF THE INVENTION

This invention relates to active acoustic attenuation systems, and more particularly, to an adaptive multi-channel system.

Active acoustic attenuation involves injecting a canceling acoustic wave to destructively interfere with and cancel an input acoustic wave. Acoustic waves include both sound waves and vibrations. In an active acoustic attenuation system, the output acoustic wave is sensed with an error transducer, such as a microphone, that supplies an error signal to an adaptive filter control model. The adaptive filter control model is normally located in an electronic controller having a central processing unit (i.e. digital signal processor) and input and output parts. The adaptive filter control model supplies a correction signal to a canceling transducer such as a loud speaker. The canceling transducer injects the canceling acoustic wave to destructively interfere with the input acoustic wave so that the output acoustic wave at the error transducer is zero or some other desired value.

In a multi-channel active acoustic attenuation system, multiple input transducers (i.e. sensors) and/or multiple canceling transducers (i.e. actuators) and/or multiple error transducers (i.e. sensors) may be used. Each channel in the adaptive filter control model normally represents a path between one of the input transducers and one of the canceling transducers. It is preferred that the channels in the control model be either intraconnected, or decoupled. Multiple input transducers may be used to provide a plurality of input signals representing the input acoustic wave to the adaptive filter control model. Multiple error transducers may be used to provide a plurality of error input signals representing the output acoustic wave to the adaptive filter control model. The error input signals are used to update each of the channels in the adaptive filter control model. In response to the input signals and/or error signals, the adaptive filter control model supplies a correction signal to each canceling transducer to inject a canceling acoustic wave.

Normally, each input transducer, each canceling transducer, and each error transducer are connected to the adaptive filter control model by a separate, distinct cable. In systems having a small number of transducers, or in systems where the transducers are closely situated to the electronic controller executing the adaptive filter control model, the number of transducer cables does not normally present a problem. However, in systems with numerous transducers; the number, weight, and cost of transducer cables can become a significant concern.

The present invention provides an adaptive multi-channel active acoustic attenuation system for attenuating complex acoustic waves. The system is especially useful for attenuating complex acoustic waves propagating in a duct, a room, a vehicle cab, an airplane, or free space. The system may be used with multiple input sensors and/or multiple canceling actuators and/or multiple error sensors and includes a controller having a communication module and a central processing unit.

One or more input sensor nodes and/or one or more error sensor nodes are also provided in the system. Each node includes a sensor and a network interface. One or more output nodes may also be provided. Each output node includes an actuator and a network interface. A medium physically interconnects each of the network interfaces to the communication module of the controller by means of a control bus or the like. A control network is provided for controlling communication between the communication module of the controller and each of the network interfaces so as to control the flow of data along the medium.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 9 is a exploded side elevational view of the connector of FIG. 6; and FIG. 10 is a side elevational view of the connector of FIG. 9.

DETAILED DESCRIPTION OF THE PREFERRED EMBODIMENT

Prior Art

Figure 1:
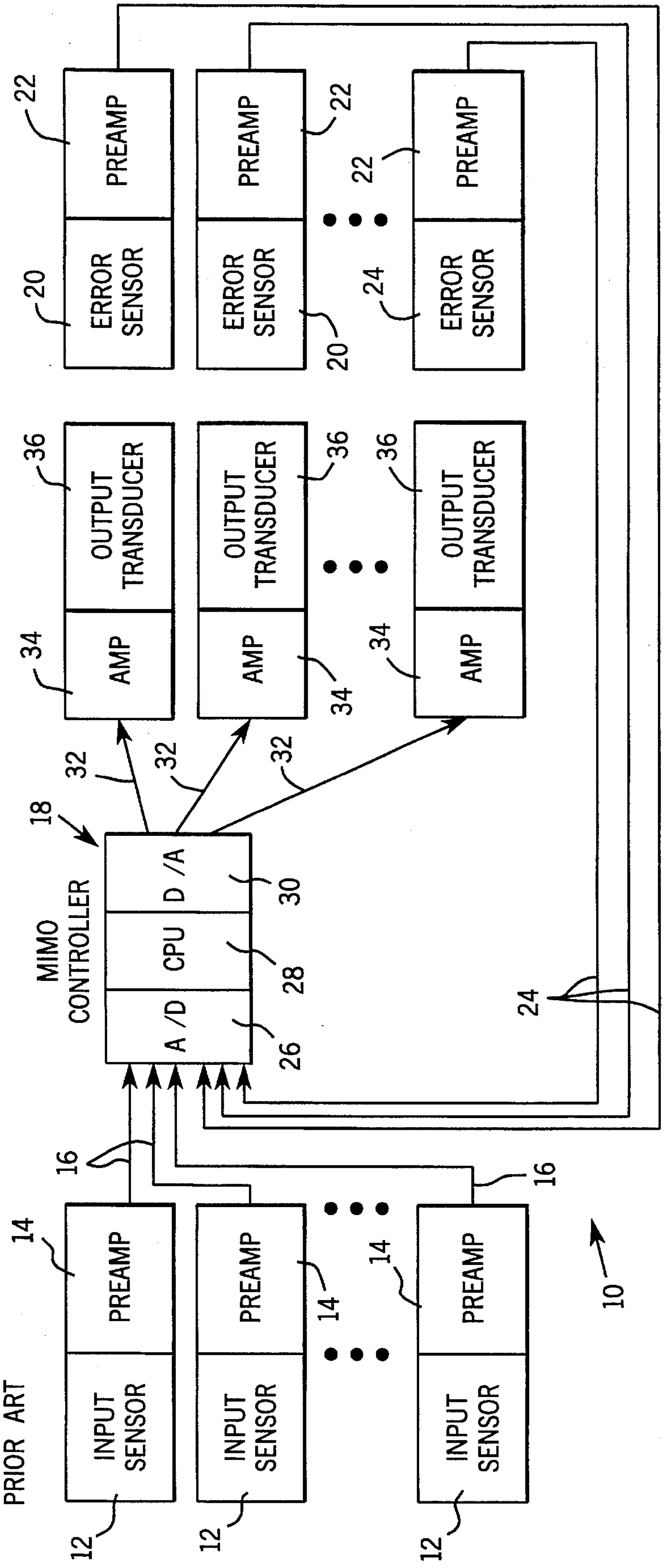
FIG. 1 PRIOR ART
FIG. 1 is a schematic illustration of a prior art adaptive multi-channel active acoustic attenuation system.

FIG. 1 is a prior art multi-channel active acoustic attenuation system and is generally designated by the reference numeral 10. System 10 includes a plurality of input sensors 12 to sense an input acoustic wave. Each input sensor provides an input signal which is amplified by preamplifier 14 and transmitted on cable 16 into a multiple-input/multiple-output (MIMO) controller 18. System 10 also includes a plurality of error sensors 20 to sense the output acoustic wave and provide an error signal. The error signal is amplified by preamplifier 22 and transmitted along cable 24 to MIMO controller 18.

MIMO controller 18 includes an analog-to-digital converter 26 which receives the plurality of input signals from input cables 16 and the plurality of error signals from cables 24 and converts these analog signals to digital signals which are provided to the central processing unit (CPU) 28 in MIMO controller 18. CPU 28 preferably includes a plurality of adaptive filter channel models, with each channel model being intraconnected to each of the remaining channel models and providing a generalized solution wherein the inputs and the outputs of all channel models depend on the inputs and outputs of all other channel models. In the alternative, the CPU 28 can include decoupled channel models.

The plurality of adaptive filter channel models in CPU 28 generate a plurality of digital correction signals which are converted to analog correction signals by a digital-to-analog converter 30 within MIMO controller 18. Each analog correction signal is transmitted along a cable 32 to a distinct amplifier 34, each of which is connected to a distinct output transducer 36.

Output transducer 36 receives the amplified analog correction signal and injects an acoustic wave to destructively interfere with the input acoustic wave and cancel same such that the output acoustic wave or sound at the error sensor is zero or some other desired value.

Present Invention

Figure 2:
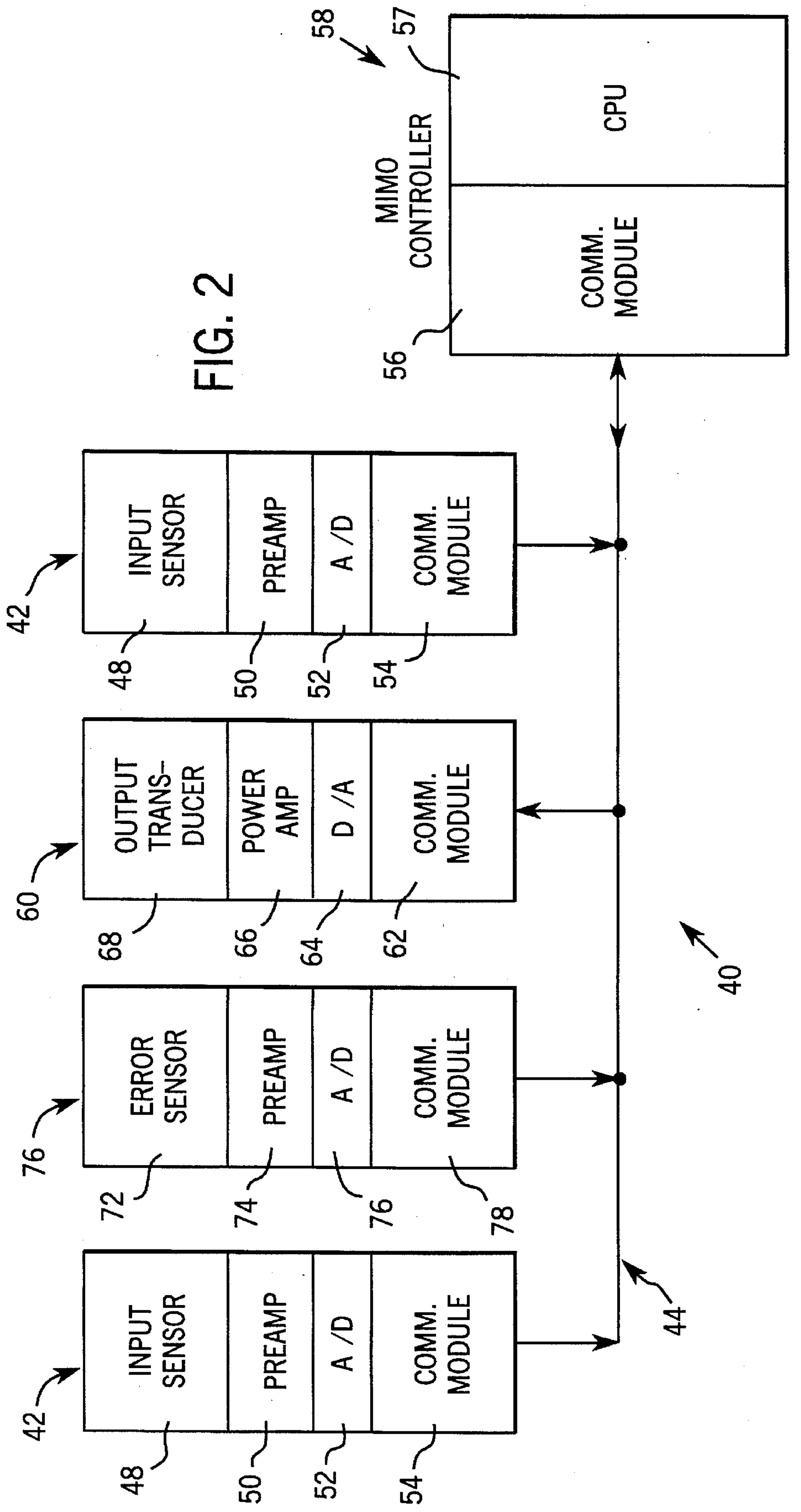
FIG. 2 is a schematic illustration of an adaptive multi-channel active acoustic attenuation system in accordance with the present invention.
Figure 6:
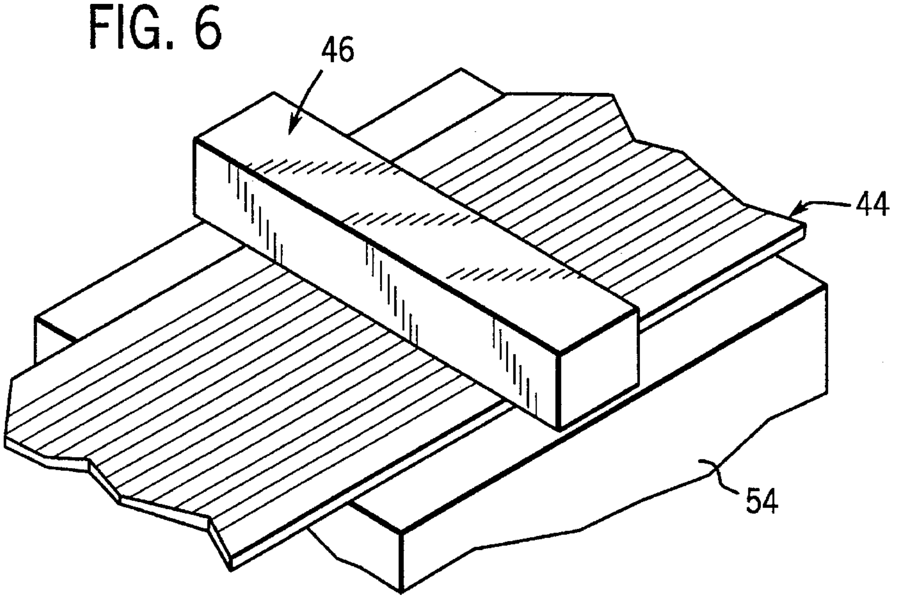
FIG. 6 is an isometric view of a connector connecting a node in the adaptive multi-channel active acoustic attenuation system of FIG. 2.
Figure 7:
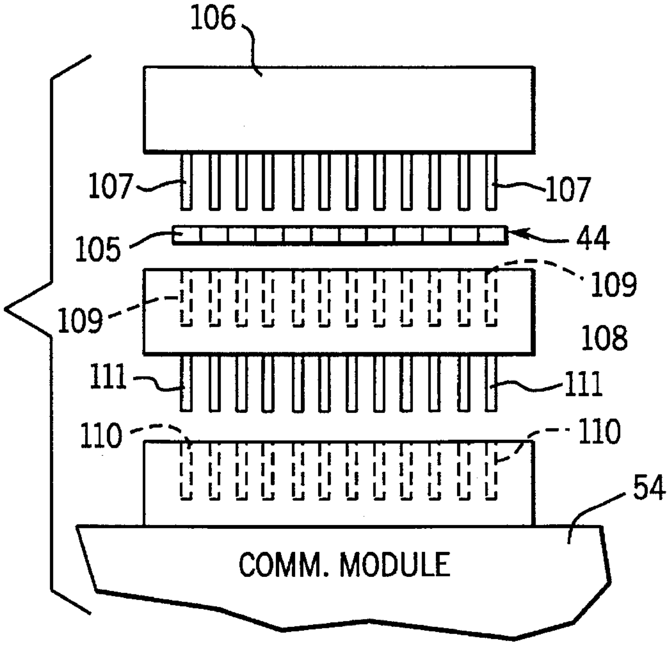
FIG. 7 is an exploded, side elevational view showing a second embodiment of a connector connecting the node of FIG. 6.
Figure 8:
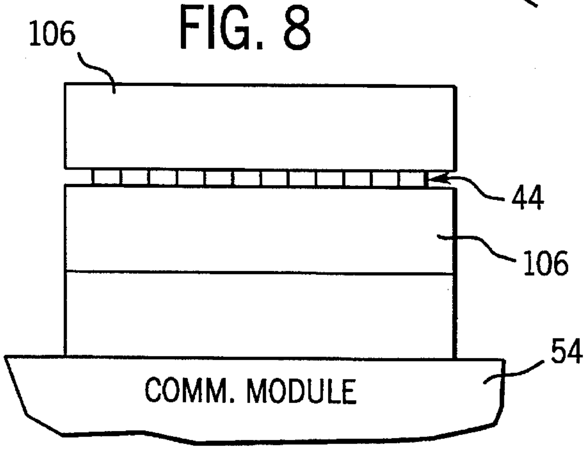
FIG. 8 is a side elevational view of the connector of FIG. 7.

FIG. 2 discloses the adaptive multi-channel active acoustic attenuation system of the present invention and is generally designated by the reference numeral 40. System 40 incorporates a network having a bus topology. System 40 includes one or more input sensor nodes 42 which are connected to a bus line 44, such as a ribbon cable or similar multi-connector cable, by connector 46, as shown in FIG. 6. Referring to FIG. 2, input sensor node 42 includes an input sensor 48, such as an input microphone or an accelerometer, for sensing the input acoustic wave and for generating an input signal in response thereto. The input signal generated by input sensor 48 is amplified by preamplifier 50 and converted from an analog signal to a digital signal by analog-to-digital converter 52 in input sensor node 42. The digital signal generated by analog-to-digital converter 52 is supplied to a network interface such as communications module 54 which communicates with a network interface such as communication module 56 of MIMO controller 58, as hereinafter described.

System 40 further includes one or more output transducer nodes 60 which receive instructions from the communication module 56 of MIMO controller 58 along bus line 44. When the network interface such as communication module 62 of each output transducer node 60 receives information from communication module 56, such as a correction signal, digital-to-analog converter 64 converts the information to an analog signal which is amplified by power amplifier 66. In response to the amplified signal, output transducer 68 introduces a canceling acoustic wave to attenuate the input acoustic wave and yield an attenuated output acoustic wave.

One or more error sensor nodes 70 are provided. Each error sensor node 70 includes an error sensor 72 which senses the output acoustic wave at the error sensor 72 and generates an analog error signal which is amplified by preamplifier 74. The amplified error signal from preamplifier 74 is converted from an analog signal to a digital signal by analog-to-digital converter 76. A digital error signal is then sent as a packet from a network interface such as communication module 78 to communication module 56 in MIMO controller 58 along bus line 44, as herein after described.

This system provides a multi-channel generalized active acoustic attenuation system for complex acoustic fields. The communication module 56 in MIMO controller 58 receives an input signal from each input sensor node 42 and an error signal from each error sensor node 70, and provides the signals to the central processing unit (CPU) 57 in MIMO controller 58. The CPU 57 executes a plurality of adaptive filter channel models in response to the input signals and the error signals received by the communication module 56. In the alternative, an input signal may be provided by one or more error signals in the case of a periodic noise source.

In the preferred embodiment, each channel model models a path between a given input and output transducer. It is preferred that each channel model implement a filtered-X LMS update algorithm (i.e. finite impulse response) or a filtered-U RLMS update algorithm (i.e. infinite impulse response), which are disclosed in U.S. Pat. Nos. 4,677,676 and 4,677,677 and incorporated herein by reference.

Each of the multiple channel models is preferably intraconnected with all of the channel models. The inputs and outputs of all channel models depend on the inputs and outputs of all other channel models. This plurality of intraconnected adaptive filter channel models is fully described in U.S. Pat. Nos. 5,216,721 and 5,216,722 which are incorporated herein by reference. Alternatively, the channel models can be decoupled.

In response to the one or more input signals and the one or more error signals, the adaptive filter channel models output a correction signal for each output transducer 68 in order to introduce the canceling acoustic wave. As a result, a distinct correction signal is sent as a packet from communication module 56 of MIMO controller 58 to each output transducer node 60.

A control network is used to connect nodes 42, 60 and 70 to MIMO controller 58 such that packets of information may be passed from input sensor nodes 42 and error sensor nodes 70 to MIMO controller 58, and from MIMO controller 58 to output transducer 60. As shown in FIG. 2, a control bus 44 is the medium that interconnects nodes 42, 60 and 70 to MIMO controller 58. The offered traffic generated by each node 42, 60 and 70 and the MIMO controller 58 along the control bus 44 must be managed so that all of the offered traffic gets through. Consequently, a protocol must be selected to control the transmission of signals on bus line 44 and to prevent possible collisions of packets. The protocol selected is dependent not only on the data rates required by nodes 42, 60, 70 and 58, but also on the maximum rate at which data may be transmitted along bus line 44 and the maximum number of nodes required by the system. Several known protocols, including IEEE-488, Token Bus and Ethernet, are sufficient. It is also contemplated that additional buses may be included, connecting all the nodes or a subset thereof, to increase communications capability.

Figure 3:
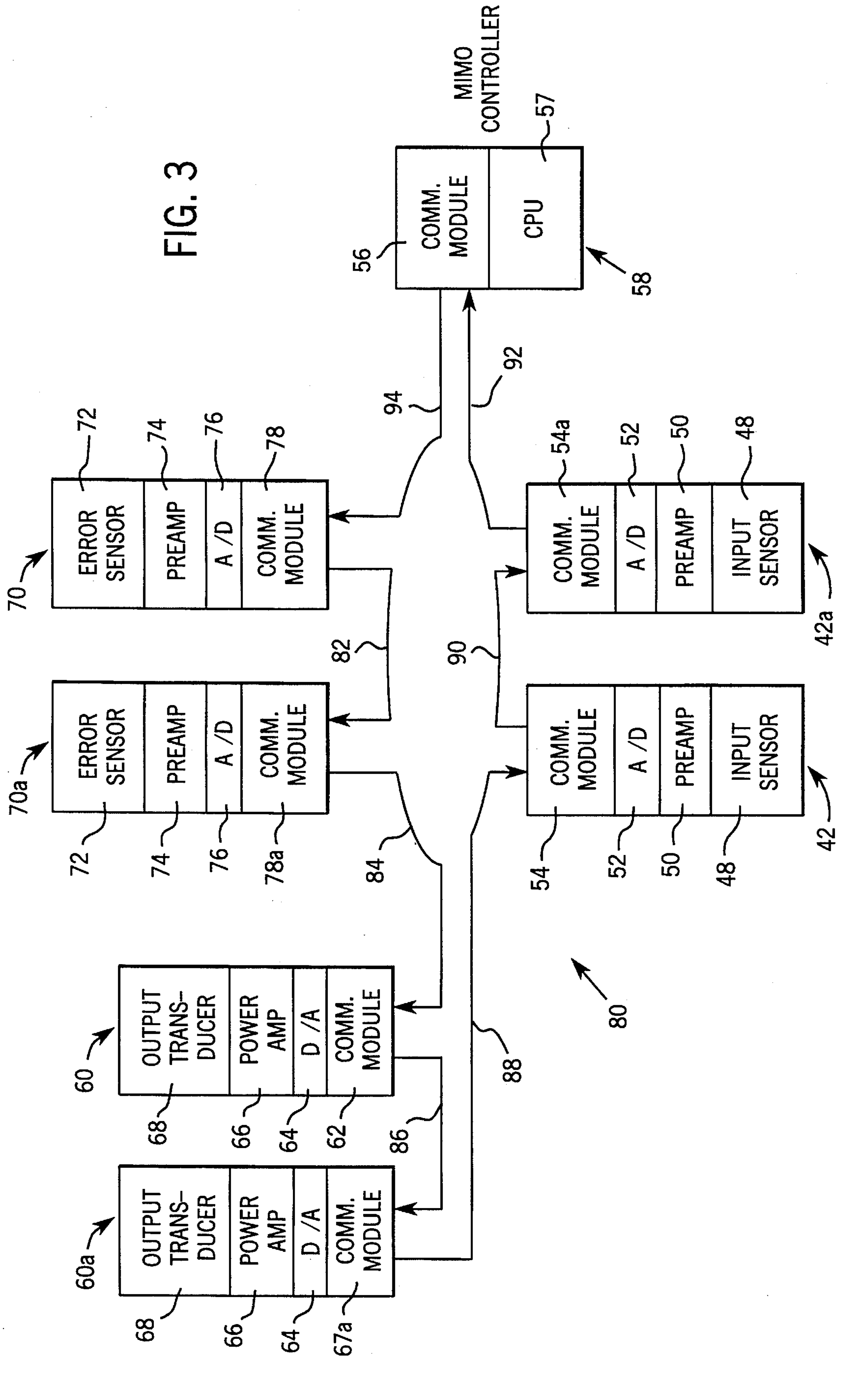
FIG. 3 is a second embodiment of an adaptive multi-channel active acoustic attenuation system of FIG. 2.

FIG. 3 discloses a second embodiment of the system of the present invention and is generally designated by the reference numeral 80. System 80 utilizes common components with the system disclosed in FIG. 2, and common reference characters will be utilized.

System 80 incorporates a ring topology instead of the bus topology used by the system described in FIG. 2. System 80 includes one or more error sensor nodes. For facilitating an understanding of system 80, a pair of error sensor nodes are shown and generally designated by the references numerals 70 and **70*a*. Each error sensor node 70, 70*a* includes an error sensor 72 that senses the acoustic wave at the error sensor 72 and generates an analog error signal which is amplified by preamplifier 74. The amplified error signal from preamplifier 74 is converted from an analog signal to a digital signal by analog-to-digital converter 76. The digital error signal generated by analog-to-digital converter 76 in error sensor node 70 is supplied to communications module 78 in error sensor node 70 for eventual transmission to MIMO controller 58; and the error signal generated by analog-to-digital converter 76 is supplied to communication module 78*a* in error sensor node 70a for eventual transmission to MIMO controller 58**.

The communication module 78 in error sensor node 70 is linked to the communication module of an adjacent node, for example, error sensor node 70a in FIG. 3, by a cable 82 on which the error signal is transmitted in response to a command by a protocol. Similarly, the communication modules 78a of error sensor node 70a is linked by cable 84 to the communication module of the next adjacent node, for example, communication module 62 in output transducer node 60. The error signal generated by error sensor 72 in error sensor node 70a may be transmitted on cable 84 to output transducer node 60 in response to a command by the protocol.

System 80 further includes one or more output transducer nodes 60 and 60a. Output transducer node 60 receives a packet from adjacent error sensor node 70a through cable 84. When communication module 62 of output transducer node 60 receives a packet of information, digital-to-analog converter 64 converts the packet to an analog signal which is amplified by power amplifier 66. In response to the amplified signal, output transducer 68 introduces a canceling acoustic wave to attenuate the input acoustic wave and yield an attenuated output acoustic wave. However, in the ring topology, output transducer node 60 may receive a packet that is directed toward another node in system 80. If the packet is not directed toward the specific node which receives the packet, the packet is forwarded by communication module 62 on cable 86 to the communication module in the next adjacent node, for example, communication module 62a of output transducer node 60a.

As previously described with respect to output transducer node 60, when communication module 62a of output transducer node 60a receives a packet of information which is directed toward output transducer node 60a, digital analog converter 64 converts the packet to an analog signal which is amplified by power amplifier 66. In response to the amplified signal, output transducer 68 introduces a canceling acoustic wave to attenuate the input acoustic wave. If output transducer node 60a receives a packet of information that is directed toward another node in system 80, the packet is forwarded by communication module 62a on cable 88 to the next adjacent node in response to a command by the protocol.

One or more input sensor nodes are also provided. To facilitate understanding, FIG. 3 shows a pair of input sensor nodes 42, 42a. Each input sensor node 42, 42a includes an input sensor 48, such as an input microphone or accelerometer, for sensing the input acoustic wave and for generating an input signal in response thereto. The input signal generated by input sensor 48 is amplified by preamplifier 50 and converted from an analog signal to a digital signal by analog-to-digital converter 52 in input sensor node 42. The digital signal generated by analog-to-digital converter 52 is supplied to communications module 54 in the case of input sensor node 42; and the input signal is supplied to communication module 54a in the case of input sensor node 42a.

Communication module 54 transmits the input signal on cable 90 to the communication module in the next adjacent node, for example, communication module 54a in input sensor node 42a, in response to a command by the protocol. Likewise, communication module 54a transmits the input signal on cable 92 to the next communication module, for example, communication module 56 in MIMO controller 58. As previously described, any packets or information received by communication module 54 from line 88 that are not directed toward input sensor node 42 are transmitted to communication module 54a in the next adjacent input sensor node 42a in response to a command by the protocol. Likewise, any packets of information received by communication module 54a that is not directed toward input sensor node 42a will be passed to communication module 56 in MIMO controller 58 in response to a command by the protocol.

As shown in FIG. 3, MIMO controller 58 is positioned within the ring of nodes 42, 42a, 60, 60a, 70 and 70a. In FIG. 3, the ring of cables, 82, 84, 86, 88, 90, 92 and 94 is the medium that connects the nodes 42, 42a, 60, 60a, 70 and 70a to MIMO controller 58. As previously described, the MIMO controller 58 includes a communication module 56 and a CPU 57. Communication module 56 receives an input signal from each input sensor node 42 and 42a and an error signal from each error sensor node 70 and 70a and in response thereto generates a correction signal on cable 94 which is directed toward a predetermined output transducer node 60 and 60a upon command by the protocol.

In response to a command by the protocol, packets of information pass from one node to the next until the information reaches a predetermined node address. The predetermined node address for the input signals and the error signals is the communication module 56 of the MIMO controller 58. The predetermined node address for the correction signal is an output transducer node 60 and 60a. The protocol must be selected to prevent possible collisions of packets, and to insure the proper node address receives the proper packet. Several known protocols, including Token Ring, FDDI, and SCI, are sufficient. It is contemplated within the scope of the invention to rearrange the nodes in any order along the ring of FIG. 3 depending upon the demands placed on system 80. It is also contemplated that additional ring(s) may be included, with packets travelling in the same or opposite direction as the first ring, to increase communication capability.

Figure 4:
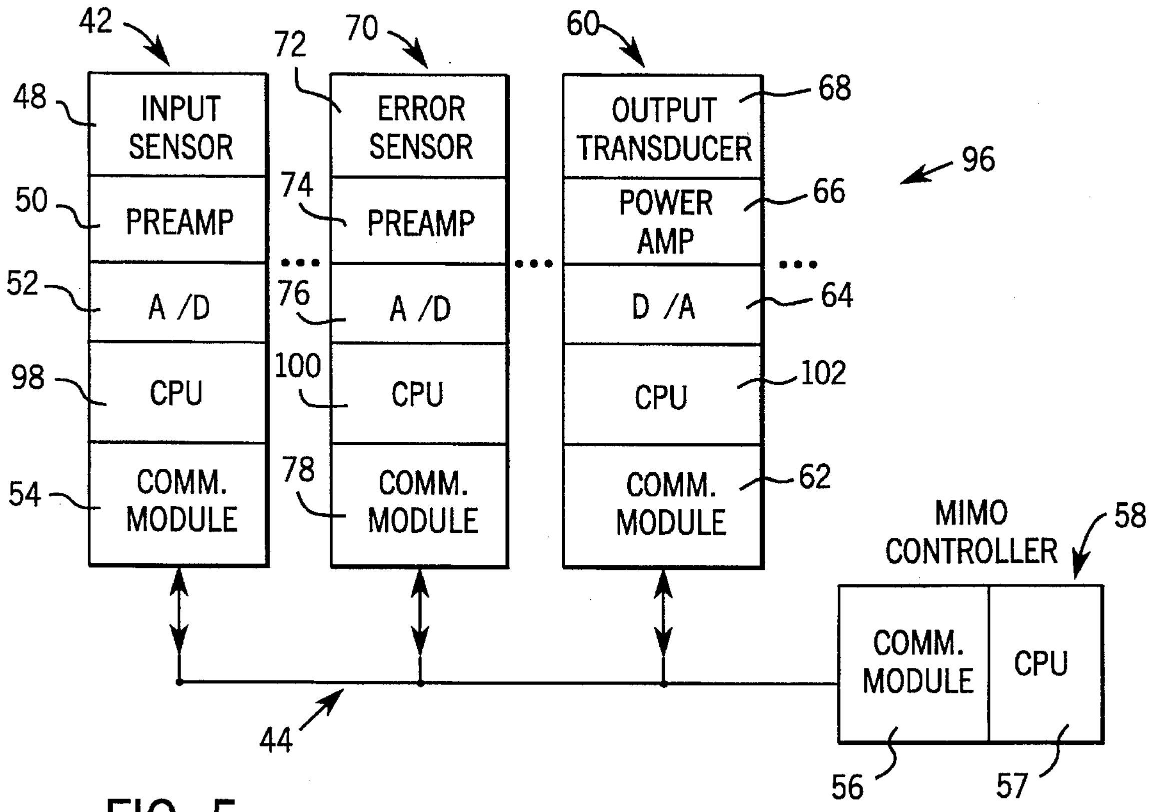
FIG. 4 is a third embodiment of an adaptive multi-channel active acoustic attenuation system of FIG. 2.
Figure 5:
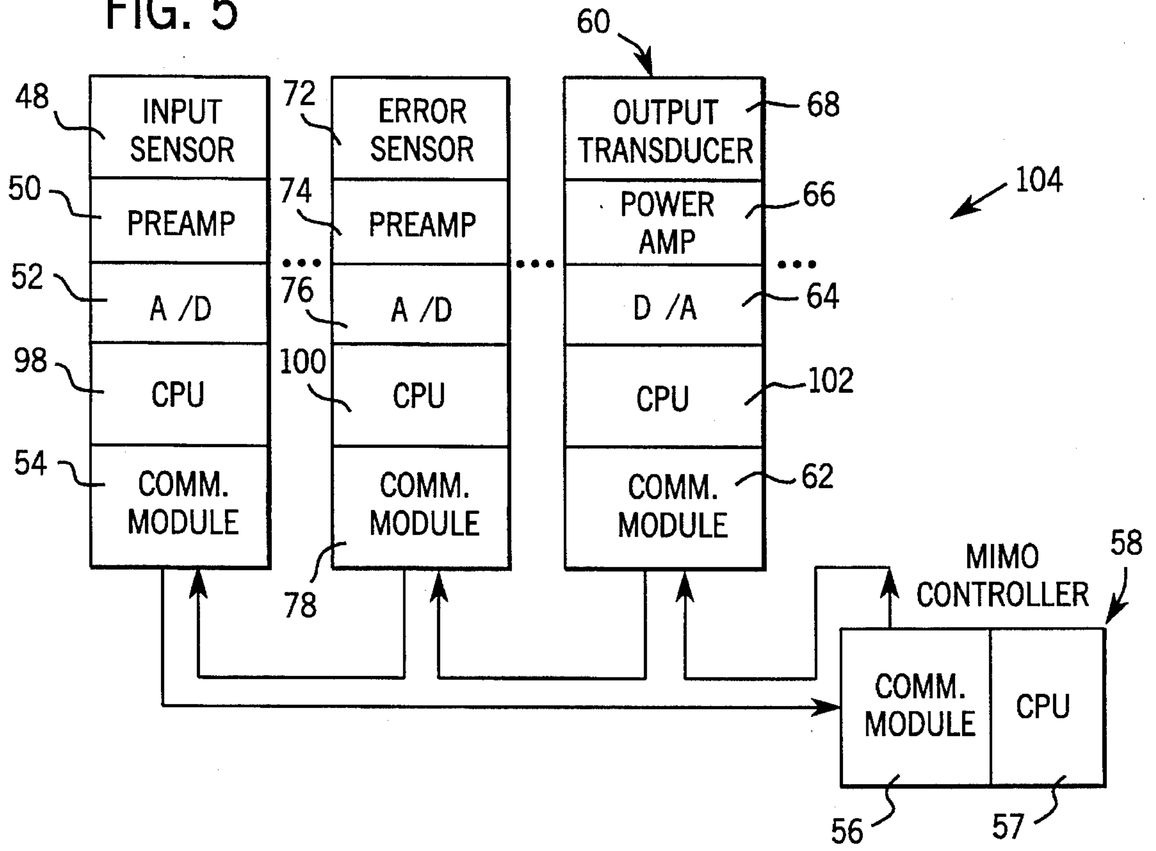
FIG. 5 is a fourth embodiment of an adaptive multi-channel active acoustic attenuation system of FIG. 2.

Referring to FIGS. 4 and 5, it is often times desirable for certain processing steps to be conducted at the node instead of passing packets of information to the controller for processing. In such a system, each node may issue commands to the other nodes, while the overall system can be governed by a master list of commands in the central processing unit 57 of the MIMO controller 58. In the alternative, each node may be an autonomous element that monitors the packets of information flowing on the bus or the ring to each of the other nodes, and thereafter decide whether to act on that information.

Referring in particular to FIG. 4, system 96 includes one or more input sensor nodes 42 that are connected to a bus line 44, such as a ribbon cable or similar multi-connector cable, using a connector such as connector 46 shown in FIG. 6. A CPU 98 is placed between the analog-to-digital converter 52 and the communication module 54. CPU 98 allows input sensor node 42 to monitor the other nodes in system 96, and to perform processing on the input signal generated by input sensor 48.

One or more error sensor nodes 70 are connected to bus line 44 using a connector 46. Each error sensor node 70 includes a CPU 100 that allows error sensor node 70 to monitor the other nodes and the information traveling on bus line 44, and allows the error sensor node 70 to process the error signal generated by error sensor 72.

Output transducer node 60 includes a CPU 102 that allows output transducer node 60 to monitor the other nodes in system 96 and the information transmitted on bus line 44.

CPU 102 can process this information to generate a correction signal, or can further process a correction signal received from the MIMO controller 58 so as to generate a more accurate canceling acoustic wave. As with system 40 described in FIG. 2, system 96 requires a protocol to be selected to control transmission of information by the nodes and to prevent possible collision of packets. Additional buses may be added to enhance communication capability.

The system 104 of FIG. 5 is similar to system 96 of FIG. 4, but system 104 incorporates the ring topology. System 104 allows each node to monitor the other nodes in the system, and allows each node to perform its predetermined function in response thereto. As with the embodiments shown in FIGS. 2–4, a protocol must be selected to prevent possible collisions of packets. Additional rings may be added to enhance communications capability.

FIGS. 6–10 show a connector 46 for connecting a communication module, for example communication module 54, of a node to a ribbon cable 44 having a plurality of parallel extending conductors 105. Connector 46 includes an upper member 106 having a plurality of terminals 107 depending therefrom. Each terminal 107 is spaced along the lower surface of the upper member 106 so as to correspond to a one-to-one relationship with the conductors 105 in the ribbon cable 44. Connector 46 may include an intermediate member 108 having a plurality of spaced terminal receipt slots 109 for receipt of the terminals 107 depending from the upper portion 106 (See FIG. 7). Each terminal slot 109 is electrically connected to a distinct, corresponding terminal 111 depending from the lower surface of the intermediate member 108.

Communication module 54 includes a plurality of spaced parallel terminal receipt slots 110 therein. Each terminal receipt slot 110 in communication module 54 corresponds to a distinct terminal 111 depending from the lower surface of intermediate member 108.

In operation, ribbon cable 44 is positioned between upper member 106 and intermediate member 108. Terminals 107 are urged through ribbon cable 44 such that each terminal 107 comes into electrical contact with one of the conductors in the ribbon cable 44 and each terminal 107 extends into a distinct, corresponding terminal receiving slot 109 in the intermediate member 108.

In order to connect the desired node to ribbon cable 44, each terminal 111 depending from the lower surface of intermediate member 108 is inserted into a distinct corresponding terminal receiving slot 110 in the communication module 54 of the node. Through this electrical connection, the node receives electrical power and is allowed to communicate with the other nodes and the controller in the system.

Referring to FIG. 9, an alternate embodiment of connector 46 is shown wherein intermediate member 108 is not present. In this alternate embodiment, each terminals 107 depending from the lower surface of the upper member 106 are received directly into a distinct, corresponding terminal receiving slot 110 in the communication module 54.

In operation, the ribbon cable 44 is positioned between the upper member 106 and the communication module 54. In order to electrically connect the ribbon cable 44 to the communication module 54, each terminal 107 depending from the upper member 106 are urged through the ribbon cable 44 so that each terminal 107 comes into electrical contact with a distinct conductor 105 in the ribbon cable 44. The terminals 107 are then urged into a distinct terminal receiving slot 110 in the communication module 54 of the desired node, thereby electrically interconnecting the node to the ribbon cable 44.

Various modes of carrying out the invention are contemplated as being within the scope of the claims.

We claim:

1. An adaptive multi-channel active acoustic attenuation system for attenuating an input acoustic wave, comprising:

one or more output nodes, each output node including a network interface and an actuator for introducing a canceling acoustic wave in response to a correction signal received by the network interface, the canceling acoustic wave attenuating the input acoustic wave to yield an attenuated output acoustic wave;

one or more error sensor nodes, each error sensor node including an error sensor for sensing the output acoustic wave and providing a respective error signal, and a network interface for transmitting the error signal;

a controller having a network interface that receives the one or more error signals and transmits the one or more correction signals to a respective output node, the controller also having a central processing unit that generates the one or more correction signals; and a control network for controlling the transmission and receipt of signals by each network interface.

2. The system of claim 1 wherein the central processing unit includes a plurality of interconnected adaptive filter channel models.

3. The system of claim 2 wherein each channel model is a finite impulse response filter.

4. The system of claim 2 wherein each channel model is a infinite impulse response filter.

5. The system of claim 1 wherein the control network includes a medium for physically tying each network interface together.

6. The system of claim 5 wherein the medium includes a bus line extending from the network interface of the controller, each network interface of the one or more output nodes and of the one or more error sensor nodes tied to the bus line.

7. The system of claim 5 wherein the control network includes a means for routing data between each network interface and a means for each network interface to logically address the data.

8. The system of claim 7 wherein the means for routing and the means for addressing the data includes a protocol.

9. The system of claim 5 wherein the network interface of the controller, each network interface of the one or more output nodes, and each one or more error sensor nodes are tied together in a ring topology.

10. The system of claim 5 further comprising a connector for connecting each network interface of the one or more output nodes and each network interface of the one or more error sensor nodes to the medium, the connector including an upper member having a plurality of terminals depending therefrom, each terminal extending through the medium and into a distinct terminal receipt slot in the network interface.

11. The system of claim 1 wherein the acoustic wave is a vibration.

12. The system of claim 1 wherein the acoustic wave is a sound wave.

13. The system of claim 1 wherein each one or more output nodes further includes a central processing unit for monitoring the transmission and receipt of signals by each network interface and processing the correction signal in response thereto.

14. The system of claim 1 wherein each one or more error sensor nodes further includes a central processing unit for monitoring the transmission and receipt of signals by each network interface and for processing the error signal in response thereto.

15. The system of claim 1 further comprising one or more input transducer nodes, each input transducer node including an input sensor for sensing the input acoustic wave and providing a respective input signal, and a network interface for transmitting the input signal.

16. A method for transmitting signals to and from a controller in an adaptive multi-channel active acoustic attenuation system for attenuating an input acoustic wave, comprising the steps of:

providing one or more output nodes, each output node including a network interface and an actuator;

generating a canceling acoustic wave by the actuator in response to a correction signal received by the network interface of the respective output node;

attenuating the input acoustic wave with the canceling acoustic wave to yield an attenuated output acoustic wave;

providing one or more error sensor nodes, each error sensor node including an error sensor and a network interface;

sensing the output acoustic wave with the error sensor and providing a respective error signal;

transmitting the error signal with the network interface;

providing a controller having a network interface and a central processing unit;

receiving the error signal with the network interface of the controller;

transmitting the error signal to the controller;

generating one or more correction signals in the central processing unit of the controller;

transmitting with the network interface of the controller the one or more correction signals to a respective output node; and controlling the transmission and receipt of each signal by each network interface.

17. The system of claim 16 further comprising the step of physically tying each network interface together with a medium.

18. The method of claim 17 further comprising the step of routing the data between each network interface.

19. The method of claim 17 further comprising the step of logically addressing the data with each network interface.

20. The method of claim 16 further comprising the steps of:

providing each output node with a central processing unit;

monitoring the transmission and receipt of the signals by each network interface with each central processing unit; and processing the respective correction signal with the central processing unit in response to the transmission and receipt of signals by each network interface.

21. The method of claim 16 further comprising the steps of:

providing each error sensor node with a central processing unit;

monitoring with each central processing unit the transmission and receipt of signals by each network interface; and processing the respective error signal with the central processing unit in response to the transmission and receipt of signals by each network interface.

* * * * *